(12) United States Patent
Keller

(10) Patent No.: US 6,734,192 B1
(45) Date of Patent: May 11, 2004

(54) TREATMENT OF VIRAL INFECTIONS

(75) Inventor: Robert H. Keller, Weston, FL (US)

(73) Assignee: MP-1 Inc., Hollywood, FL (US)

( * ) Notice: Subject to any disclaimer, the term of this patent is extended or adjusted under 35 U.S.C. 154(b) by 50 days.

(21) Appl. No.: 09/644,414

(22) Filed: Aug. 23, 2000

Related U.S. Application Data

(60) Provisional application No. 60/150,261, filed on Aug. 23, 1999.

(51) Int. Cl.$^7$ .................. A61K 31/47; A61K 31/277
(52) U.S. Cl. .................. 514/311; 514/299; 514/183; 546/134
(58) Field of Search ................ 514/311, 299, 514/183, 27; 546/134

(56) References Cited

U.S. PATENT DOCUMENTS

| | | | |
|---|---|---|---|
| 4,795,641 A | | 1/1989 | Kashdan |
| 4,897,403 A | | 1/1990 | Martin et al. |
| 5,049,389 A | | 9/1991 | Radhakrishnan |
| 5,053,419 A | * | 10/1991 | Lipton |
| 5,380,747 A | | 1/1995 | Medford et al. |
| 5,403,574 A | | 4/1995 | Piwnica-Worms |
| 5,430,039 A | | 7/1995 | Roberts-Lewis et al. |
| 5,503,984 A | | 4/1996 | Chu et al. |
| 5,543,423 A | | 8/1996 | Zelle et al. |
| 5,597,809 A | | 1/1997 | Dreyer |
| 5,621,002 A | | 4/1997 | Bosslet et al. |
| 5,700,461 A | | 12/1997 | Schwartz |
| 5,700,781 A | | 12/1997 | Harris |
| 5,707,616 A | | 1/1998 | Grabstein et al. |
| 5,708,025 A | | 1/1998 | Samid |
| 5,719,147 A | | 2/1998 | Dorn et al. |
| 5,719,197 A | | 2/1998 | Kanios et al. |
| 5,747,469 A | | 5/1998 | Roth et al. |
| 5,747,532 A | | 5/1998 | Lai |
| 5,747,540 A | | 5/1998 | Coburn et al. |
| 5,750,493 A | | 5/1998 | Sommadossi et al. |
| 5,756,477 A | | 5/1998 | Hovanessian et al. |
| 5,763,417 A | | 6/1998 | Einck |
| 5,763,442 A | | 6/1998 | Medlen et al. |
| 5,776,966 A | | 7/1998 | North |
| 5,786,344 A | | 7/1998 | Ratain |
| 5,821,260 A | | 10/1998 | Medford et al. |
| 5,833,994 A | | 11/1998 | Wheelock et al. |
| 5,840,711 A | | 11/1998 | Gallicchio |
| 5,840,893 A | | 11/1998 | Bukrinsky et al. |
| 5,843,979 A | | 12/1998 | Wille et al. |
| 5,846,959 A | | 12/1998 | Medford et al. |
| 5,885,786 A | | 3/1999 | Cabot |
| 5,905,068 A | | 5/1999 | Chen et al. |
| 5,914,331 A | | 6/1999 | Liotta et al. |
| 6,399,654 B1 | * | 6/2002 | Lin et al. |

FOREIGN PATENT DOCUMENTS

WO    WO 92/01451    *   2/1992

OTHER PUBLICATIONS

Journal of Infectious Diseases (1991), 164 (1), 53–60.*
Khalid et al.(Journal of Ethnopharmacology, 1986, 15 (2), 201–9.*
"Chloroquine inhibits HIV–1 replication in human peripheral blood lymphocytes", William M. Pardridge, Jing Yang, Amadou Diagne, from Immunology Letters 64 (1998), pp. 45–47.
"Effect of the Calcium Channel Blocker Verapamil on Human Immunodeficiency Virus Type 1 Replication in Lymphoid Cells", Mary Alice Harbison, Sunyoung Kim, Jacqueline M. Gillis, and Scott M. Hammer, from The Journal of Infectious Diseases 164 (1991), pp. 53–60.
"Hydroxychloroquine Treatment of Patients with Human Immunodeficiency Virus Type 1", Kirk Sperber, Michael Louie, Thomas Kraus, Jacqueline Proner, Erica Sapira, Su Lin, Vera Stecher and Lloyd Mayer, from Clinical Therapeutics Vol 17, No. 4, 1995, pp. 622–636.
"Inhibitors of human immunodeficiency virus integrase" Mark R. Fesen, Kurt W. Kohn, Francois Leteurtre, and Yves Pommier, from Proc. Natl. Acad. Sci, USA, Vol. 90, Mar. 1993, pp. 2399–2403.
"Strategies for Antiviral Therapy Based on the Retroviral Life Cycle" by Lynn Connolly, Morgan Jenkins, from The Aids Knowledge Base website http://hivinsite.ucsf.edu/akb/1994/3–5/ published Jan. 1994, pp. 1–28.

* cited by examiner

Primary Examiner—Samuel Barts
Assistant Examiner—Michael C. Henry
(74) Attorney, Agent, or Firm—Frommer Lawrence & Haug LLP; Ronald R. Santucci

(57) ABSTRACT

A pharmaceutical composition comprising therapeutically effective quantities of calcium channel blockers in combination with quinolines. In preferred embodiments, the invention further comprises quercetin. The components combine and interact in a manner to effectively treat viral infections.

2 Claims, 3 Drawing Sheets

TREATMENT OF VIRAL INFECTIONS

CROSS REFERENCE TO RELATED APPLICATIONS

This application claims priority to Application Ser. No. 60/150,261, filed Aug. 23, 1999, the contents of which are incorporated herein by reference.

BACKGROUND OF THE INVENTION

This invention relates to methods and compositions for treating viral infections including retroviruses such as HIV and Hepatitis C in mammals.

The disease now known as acquired immunodeficiency syndrome (AIDS) was first recognized as early as 1979. The number of cases reported to the Centers for Disease Control and Prevention (CDC) increased dramatically each year since then, and in 1982 the CDC declared AIDS a new epidemic. It has also been estimated that over 40 million people have been diagnosed with AIDS.

Retroviruses were proposed as the causative agent of AIDS. Recently, human immunodeficiency virus type 1 (HIV) has emerged as a preferred name for the virus responsible for AIDS. Antibodies to HIV are present in over 80% of patients diagnosed as having AIDS or pre-AIDS syndrome, and it has also been found with high frequency in identified risk groups.

AIDS is characterized by a compromised immune system attributed to the systemic depletion of CD4+T lymphocytes (T cells) and the unresponsiveness and incompetence of remaining CD4+T cells. The level of CD4+T cells serves as a diagnostic indicator of disease progression. HIV infected CD4+T cells are known to be directly cytopathic to other CD4+T lymphocytes and this single cell killing event is initiated via HIV envelope protein (gp120/41) interaction with the CD4 molecule. Highly virulent isolates of HIV induce syncytia (defined as >4 nuclei within a common cell membrane), a process associated with rapid loss of CD4+T cells and disease progression.

HIV-I infection in humans causes general immunosuppression and involves other disorders, such as blindness, myelopathy, or a dementing neurological disorder, i.e., the AIDS dementia complex, the latter of which is a common and important cause of morbidity in patients in advanced stages of infection. HIV-I infection has been documented in various areas of the CNS, including the cerebral cortex, spinal cord, and retina. Price et al. (1988, Science 239:586) and Ho et al. (1989, Annals in Internal Medicine 111:400) review the clinical, epidemiological, and pathological aspects of the AIDS dementia complex, and suggest that the mechanism underlying the neurological dysfunction may be indirect tissue damage by either viral- or cellular-derived toxic substances released by infected cells. The contents of these references is incorporated herein by reference.

There is considerable difficulty in diagnosing the risk of development of AIDS. AIDS is known to eventually develop in almost all of the individuals infected with HIV.

A patient is generally diagnosed as having AIDS when a previously healthy adult with an intact immune system acquires impaired T-cell immunity. The impaired immunity usually appears over a period of 18 months to 3 years. As a result of this impaired immunity, the patient becomes susceptible to opportunistic infections, various types of cancers such as Kaposi's sarcoma, non-Hodgkins Lymphoma and other disorders associated with reduced functioning of the immune system.

HIV replicates through a DNA intermediate. Each virus particle contains two identical, single-stranded RNA molecules surrounded by the viral nucleocapsid protein. The remaining core of the virus is composed of the capsid and matrix proteins. Enzymes required for replication and integration of the viral genetic materials into the host cells are also contained within the capsid. The outer coat of the virus particle consists of viral envelope glycoproteins and membrane derived from the host cell.

No sufficiently effective treatment capable of preventing the disease is available, although HAART (highly active anti-retroviral therapy) has reversed the immunodeficiency of AIDS. Essentially all patients with opportunistic infections and approximately half of all patients with Kaposi's sarcoma have died within two years of diagnosis. Attempts at reviving the immune system in patients with AIDS have so far been substantially unsuccessful.

While 3'-azido-3'-deoxythymidine (AZT) has been most often used in treating HIV infection and AIDS, it has considerable negative side effects such as reversible bone marrow toxicity, and the development of viral resistance to AZT by the patient. Thus other methods of treatment are highly desirable.

Viruses traditionally do not respond to antibiotic therapy. Therefore, other treatments are used when treating viral infections. One such recently discovered therapy revolves around the use of protease inhibitors to disrupt the viral replication cycle. Protease inhibitor therapy has the potential to be used in the treatment of a wide range of diseases, including viral infections, such as those caused by retroviruses (e.g., HIV), hepadnaviruses (e.g., hepatitis C virus), herpesviruses (e.g., herpes simplex virus and cytomegalovirus) and myxoviruses (e.g., influenza virus), as well as parasitic protozoa (e.g., cryptosporidium and malaria), in cancer chemotherapy and various pathological disorders. However, the protease inhibitors used in HAART have resulted in significant complications including lipodystrophy, hepetic failure and coronary artery disease.

Accordingly, it is desireable to provide improved compositions and methods for the treatment of viral infections, including retroviruses such HIV and hepatitis C.

SUMMARY OF THE INVENTION

Generally speaking, the invention involves the administration of a therapeutically effective amount of a pharmaceutical composition, and the composition itself, which is composed of therapeutically effective proportions and quantities of calcium channel blockers (or metabolites thereof) in combination with a quinolines, quinoline-quinones or intermediates or derivatives such as chloroquine. In preferred embodiments, the invention further comprises quercetin or one of its active components. The components combine and interact in a manner to effectively treat retroviruses by reducing viral activity in infected cells.

Accordingly, it is an object of this invention is to provide a safe and effective treatment for viruses such as HIV.

BRIEF DESCRIPTION OF THE DRAWINGS

For a fuller understanding of the invention, reference is had to the following description taken in connection with the accompanying drawings, in which.

DETAILED DESCRIPTION OF THE PREFERRED EMBODIMENTS

Figure 1:
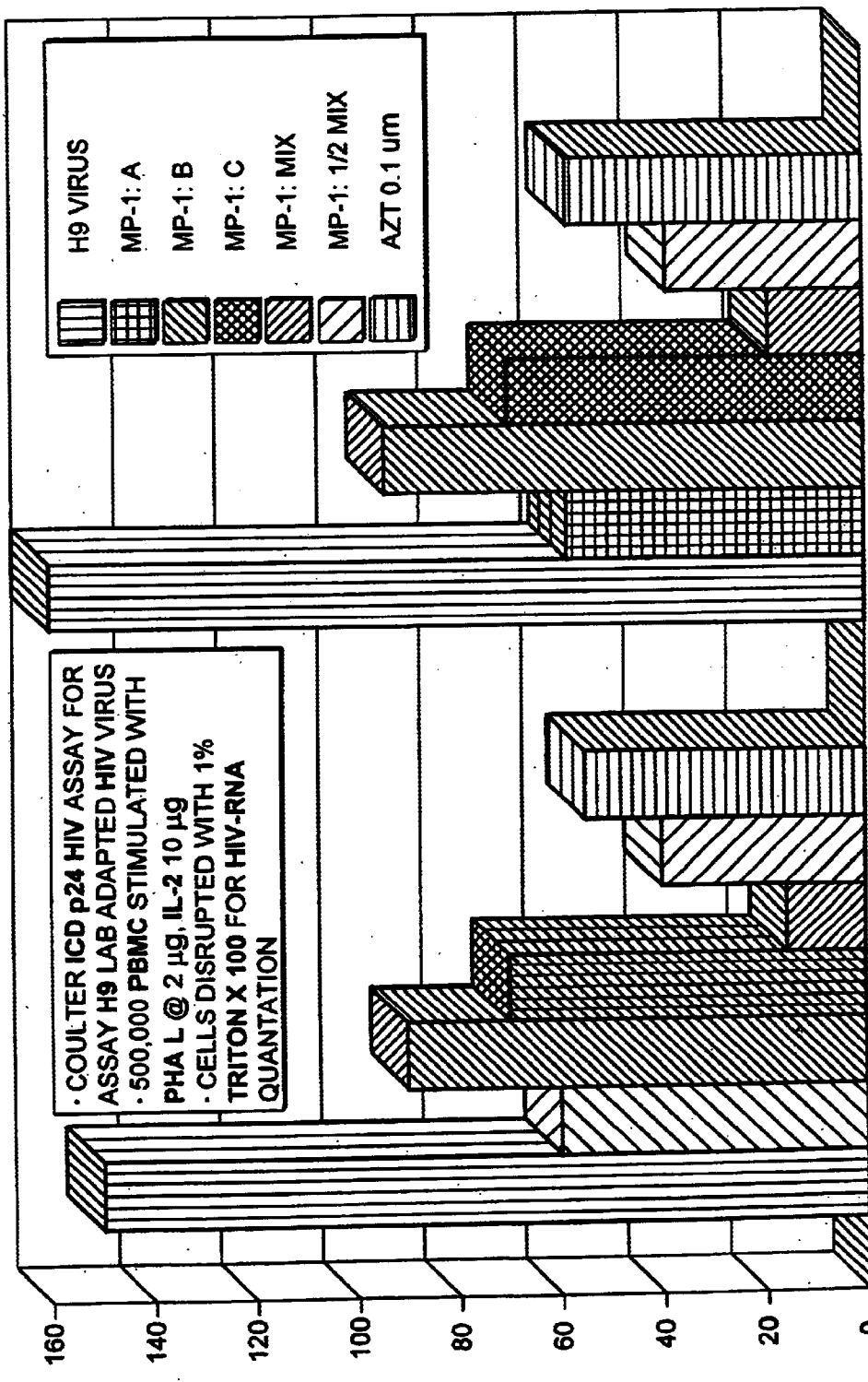
FIG. 1 is a graph depicting the results from 100 experiments on the effects of a composition in accordance with the invention on the viral load (measured by $P_{24}$ ICD) of peripheral blood lymphocytes infected with a laboratory adapted HIV virus ($H_9$)

It has been determined that administration of calcium channel blockers (or metabolites thereof) in combination with a quinoline, quinoline-quinone or intermediates or derivatives such as chloroquine, can be therapeutically effective in treating viral infection. In preferred embodiments, the invention further comprises the administration of quercetin or one of its active components. Compositions including the active ingredients recited above can be effective in reducing viral activity in mammals. It is preferred that each component be present at a weight ratio of 10 to 20 parts Ca channel blocker to about 3–8 parts quinoline, quinoline/quinone or intermediate to about 1–4 parts quercetin. As used herein, the identification of a drug or other therapeutic compound is intended to also refer to the pharmaceutically effective forms of the drug, such as the salts, hydrochlorides, chelates and so forth to establish sustained release of one or more of the active ingredients, which are used in the administration of the drug.

Research conducted in the areas of eukaryotic cell cycle control and apoptosis has found that the two events are closely linked. Furthermore, many enzymes and transcription factors that function in promoting cellular growth also appear to participate in cell death. These include Nkfb, TAR, c-Myc, p53, cyclin dependent kinases, and cyclin proteins, Bcl-2, and Bax. As already mentioned, HIV-induced cytopathicity has also been shown to invoke alterations in the phosphorylation state and/or the expression of CDK1 and cyclin B. Other stimuli that activate programmed cell death also produce aberrant expression and activation of the cyclin dependent kinases.

It has been determined that calcium channel blockers can have a positive treatment effect on AIDS infected patients. In vitro studies of the effect of calcium channel blockers on HIV infection both in HIV adapted cell lines (HUT/H9) as well as acutely infected peripheral blood lymphocytes were instituted. In aggregate, these experiments revealed a 50–60% reduction in HIV production (HIV PCR RNA) and ICD P24 antigen at pharmacologically achievable concentrations.

These results are supported by other research on calcium channel blockers. It was demonstrated that inhibition of calcium (Ca) influx during cell activation by blocking voltage regulated Ca channels results in decreased symptoms in patients suffering from hyperactive immune systems. It has also been demonstrated that voltage regulated Ca++ channel blockage significantly reduces debilitating symptoms in CFIDS. In addition, there was a concordant decrease in T cell activation without any change in immune effect or mechanisms (NK cytotoxicity, IgG levels). This decreased activation involves decreased interleukin synthesis and decreased mitogen reactivity.

QUINOLINES

The addition of quinolines, such as quinoline-quiones, or intermediates thereof, such as chlorquine, have demonstrated synergistic effects when combined with calcium channel blockers.

Chloroquine and its analogues, including hydroxychloroquine have been shown to inhibit a variety of viral infections as well as reduce immune reactivity. Both effects are mediated by a change in intracellular pH which inhibits viral, as well as cellular enzymes involved in activation. Hydroxychloroquine (HCQ), an antimalarial agent, can be used to treat patients with autoimmune disease, and can suppress human immunodeficiency virus type 1 (HIV-1) replication in vitro in T cells and monocytes by inhibiting post-transcriptional modification of the virus.

Chioroquine is one of the drugs of choice for treating acute malaria, caused by sensitive strains. Chloroquine kills the merozoites, thereby reducing the parasitemia, but does not affect the hypnozoites of P vivax and P ovale in the liver. These are killed by primaquine, which should be used to prevent relapses.

Chloroquine, which can be administered in solid or liquid form, combined with known pharmaceutically effective carriers, is a synthetic 4-aminoquinoline typically formulated as the phosphate salt for oral use and as the hydrochloride for parenteral use. The salts, hydochlorides, chelates and other forms of the active ingredients described herein will be encompassed by the term derivatives. Thus, compositions in accordance with the invention can include chloroquine and derivitives thereof.

Chloroquine is rapidly and almost completely absorbed from the gastrointestinal tract, reaches maximum plasma concentrations (50–65%) protein-bound in about 3 hours, and is rapidly distributed to the tissues. Because it is concentrated in the tissues, it has a very large apparent volume of distribution of about 13,000 L. From these sites, it is slowly released and metabolized. The drug readily crosses the placenta. It is excreted in the urine with a half-life of 3–5 days. Renal excretion is increased by acidification of the urine.

Because of its very large volume of distribution, a loading dose should be given when an effective schizonticidal plasma level of chloroquine is urgently needed in the treatment of acute attacks. To avoid life-threatening toxicity when chloroquine is given parenterally, it should be provided by slow intravenous infusion or by small incremental doses intramuscularly. A therapeutically effective plasma concentration appears to be approximately 30 $\mu$g/L against sensitive p falciparum and 15 $\mu$g/L against P vivax.

Chloroquine is rapidly and completely absorbed following oral administration. Usually 4 days of therapy suffice to cure the disease. The drug concentrates in erythrocytes, liver, spleen, kidney, and lung as well as leukocytes. Thus it has a very large volume of distribution. It persists in erythrocytes. The drug also penetrates into the central nervous system and traverses the placenta. Chloroquine is dealkylated by the hepatic mixed function oxidases, but some metabolic products retain anti-malarial activity. Both parent drug and metabolites are excreted predominantly in the urine. Excretion rate is enhanced as urine is acidified.

Chloroquine is a highly effective blood schizonticide and is the 4-aminoquinoline most widely used in chemoprophylaxis and in treatment of attacks of vivax, ovale, and malaria. Chloroquine is not active against the preerythocytic plasmodium and does not effect radical cures of p vivax or P ovale infections because it does not eliminate the persisting liver stages of those parasites.

The exact mechanism of antimalarial action has not been determined. Chloroquine may act by blocking the enzymatic synthesis of DNA and RNA in both mammalian and protozoal cells and forming a complex with DNA that prevents replication or transcript to RNA. Within the parasite, the drug concentrates in vacuoles and raises the pH of these organelles, interfering with the parasite's ability to metabolize and utilize erythrocyte hemoglobin. The drug may also decrease DNA synthesis in the parasite by disrupting the tertiary structure of the nucleic acid. Interference with phospholipid metabolism within the parasite has also been proposed. Selective toxicity for malarial parasites depends on a chloroquine-concentrating mechanism in parasitized cells. Chloroquine's concentration in normal erythrocytes is 10–20 times that in plasma; in parasitized erythrocytes, its concentration is about 25 times that in normal erythrocytes.

Patients usually tolerate chloroquine well when it is used for malaria prophylaxis (including prolonged use) or treatment. Gastrointestinal symptoms, mild headache, pruritus, anorexia, malaise, blurring of vision, and urticaria are not uncommon. Taking the drug after meals may reduce some adverse effects. Rare reactions include hemolysis in G6PD-deficient persons, impaired hearing, confusion, psychosis, convulsions, blook dyscrasias, skin reactions, alopecia, bleaching of hair, and hypotension.

Chloroquine is contraindicated in patients with a history of liver damage, alcoholism, or neurologic or hematologic disorders. Certain antacids and anti-diarrheal agents (kaolin, calcium carbonate, and magnesium trisilicate) interfere with the absorption of chloroquine and should not be taken within about 4 hours before or after chloroquine administration.

Quinine, a bitter-tasting alkaloid, is rapidly absorbed, reaches peak plasma levels in 1–3 hours, and is widely distributed in body tissues. Approximately 80% of plasma quinine is protein-bound; red blood cell 5 levels are about 20% of the plasma level and cerebrospinal fluid concentrations about 7%. The elimination half-life of quinine is 7–12 hours in normal persons but 8–21 hours in malaria-infected persons in proportion to the severity of the disease. Approximately 80% of the drug is metabolized in the liver and excreted for the most part in the urine. Excretion is accelerated in acid urine.

With constant daily doses, plasma concentrations usually reach a plateau on the third day. In normals or in mild infection, standard oral doses result in plasma levels of about 7 $\mu$g/mL; in severe malaria, higher plasma levels are reached. A mean plasma concentration of over about 5 $\mu$g/mL is effective to eliminate asexual parasites of vivax malaria and a somewhat higher concentration in falciparum malaria. Concentrations lower than 2 $\mu$g/mL have little effect, whereas concentrations over 7 $\mu$g/mL are generally accompanied by adverse reactions of "cinchonism." Because of this narrow therapeutic range of about 2–7 $\mu$g/mL, adverse reactions are common during quinine treatment of falciparum malaria.

Quinine is a rapidly acting, highly effective blood schizonticide against the four malaria parasites. The drug is gametocidal for P vivax and P ovale but not very effective against p falcimparum gametocytes. Quinine has no effect on sporozoites or the liver stages of any of the parasites.

The drug's molecular mechanism is unclear. Quinine is known to depress many enzyme systems. It also forms a hydrogen-bonded complex with double-stranded DNA that inhibits strand separation, transcription, and protein synthesis.

Mefloquine is used in prophylaxis and treatment of chloroquine-resistant and multidrug-resistant falciparum malaria. It is also effective in prophylaxis against P vivax and presumably against P ovale and P malaria.

Mefloquine hydrochloride is a synthetic 4-quinoline methanol derivative chemically related to quinine. It is generally only given orally because intense local irritation can occur with parenteral use. It is well absorbed, and peak plasma concentrations are reached in 7–24 hours. A single oral dose of 250 mg of the salt results in a plasma concentration of 290–340 ng/mL, whereas continuation of this dose daily results in mean steady state plasma concentrations of 560–1250 ng/mL. Plasma levels of 200–300 ng/mL may be necessary to achieve chemo-suppression in P falciparuminfections. The drug is highly bound to plasma proteins, concentrated in red blood cells, an dextensively distributed to the tissues, including the central nervous system.

Mefloquine is cleared in the liver. Its acid metabolites are slowly excreted, mainly in the feces. Its elimination half-life, which varies from 13 days to 33 days, tends to be shortened in patients with acute malaria. The drug can be detected in the blood for months after dosing ceases.

Primaquine phosphate is a synthetic 8-aminoquinoline derivative. After oral administration, the drug is usually well absorbed, reaching peak plasma levels in 1–2 hours, and then is almost completely metabolized and excreted in the urine. Primaquine's plasma half-life is 3–8 hours and its peak serum concentration is 50–66 ng/mL; trace amounts to the tissues, but only a small amount is bound there.

Its major metabolite is a deaminated derivative, carboxyprimaquine, that reaches plasma concentrations more than ten times greater than those of the parent compound, is eliminated slowly (half-life 22–30 hours), and accumulates with daily dosing; peak serum concentrations after 14 daily doses are 432–1240 ng/mL. Whether primaquine or one of its metabolites is the active compound has not been determined.

The mechanism of primaquine's antimalarial action is not well understood. The quinoline-quinone intermediates derived from primaquine are electron-carrying redox compounds that can act as oxidants. These intermediates probably produce most of the hemolysis and methemoglobinemia associated with primaquine's use.

QUERCETIN

Quercetin [2-(3,4-Dihydroxyphenyl)-3,5,7-trihydroxy-4H- 1 -benzopyran-4-one] and derivatives thereof is a natural flavanoid and is used for its ability to eliminate toxic compounds found in the liver. It has anti-hepatotoxic, antiviral, anti-inflammatory and antibacterial properties. It may be synthesized by the method of Shakhova et al., Zh. Obsheh. Khim., 32, 390 (1962), incorporated by reference. Quercetin an inhibit bonding of HIV to $CD_4$ as well as both viral intergase and viral reverse transcriptase and has also been shown to inhibit HIV activity.

Quercetin is a naturally occurring flavone, often found in plant material that is consumed by animals, including humans, on a daily basis. Quercetin, a common constituent of plants, was identified from a TCM extract that was determined to be a Ah receptor antagonist. The chemical configuration of Quercetin, like flavones generally, is composed of two benzene rings linked through a heterocyclicpyrine ring. Quercetin has been shown to be a genotoxic compound, that may initiate carcinogenic activity in certain tissues if administered at high dosages over a prolonged period.(Dunnick, J. K., and Hailey, J. R. 1992, incorporated herein by reference). It has been demonstrated that when in the presence of already transformed cells Quercetin has an anti-proliferative effect on those transformed, cancerous cells. (Scambiaet al., 1993, incorporated herein by reference).

Compositions of matter, in accordance with preferred embodiments of the invention can comprise in admixture: a calcium channel blocker; a quinoline; quercetin; derivatives of these components, such as pharmaceutically acceptable salts, hydrochlorides chelates and metabolites thereof and a pharmaceutically acceptable systemic carrier for oral administration. The invention also comprises a combination of the metabolites of these three components. The components can be provided in solid or liquid form, as particle suspensions or in water or alcohol based solutions. The compositions can be formulated for oral or parentenal administration, although oral administration is preferred. The components of the composition should be provided in therapeutically effective amounts to treat viruses, such as HIV. In a weight/conc. ratio of about 10–20 Ca channel blocker (or metabolite): about 3–8 chloroquine, quinoline, quinoline/quinone: about 1–4 quercetin.

The invention also comprises administration of a composition in accordance with preferred embodiments of the invention to a mammal suffering from a viral infection such as HIV, in sufficient dosage to reduce and treat such infection.

It has been demonstrated that inhibition of calcium (Ca) influx during cell activation by blocking voltage regulated Ca channels results in decreased symptoms in patients suffering from hyperactive immune systems. This decreased activation involves decreased interleukin synthesis and decreased mitogen reactivity. In vitro studies of the effect of Ca channel blockers on HIV infection both in HIV adapted cell lines (HUT/H9) as well as acutely infected peripheral blood lymphocytes revealed a 50–60% reduction in HIV production (HIV PCR RNA) and ICD P24 antigen at pharmacologically achievable concentrations. A second, noncompetitive complementary class of drugs was sought which would provide an additive or resulting synergistic effect.

In experiments similar to those described above, the addition of effective amounts of Chloroquine to either H4T infected cells and acutely infected PBMC, Chloroquine reduced viral activity (replication) by 20–40%. In similar cultures with pharmacologically achievable concentrations of both verapamil, a calcium blocker and chloroquine, viral activity was reduced by 75–85%. In concert with a Ca channel blocker therefore, the net effect is to reduce the activation of NKFB from the cell as well as the HIV TAT engine and suspend the uncoated virus in the hostile milieu of the cytosol. It has been shown in multiple studies that un-translated, unintegrated virus is most susceptible to degradation and the longer the virus remains in this vulnerable state, the less replication competent it becomes.

In experiments similar to those described above, a standardized extract of quercetin (containing 1–10 μg/ml quercetin available from Sigma Alcrich) revealed a 5–20% reduction of HIV activity. When added to preferred concentrations (30 μg/ml of Verapamil and 10 μg/ml chloroquine) the composition achieved a 85–95% reduction of HIV activity. It is believed that quercetin decreases viral activity by weakly inhibiting $CO_4$ binding as well as the conversion of RNA to DNA preventing integration of the viral DNA in the genome. This occurred in a non cytotoxic manner with concentrations in vitro which are easily achievable in vivo and resulting in at least a two log decrease in viral activity. This is a much larger decrease in comparison to current R transverse inhibitors such as AZT, D4T, DDI where the viral activity decreases 4–7log.

This discovery of meaningful interaction between Ca channel blockers and chloroquine and its analogues as well as the benign side effect profile of quercetin represents a safe and potentially effective inexpensive alternative to current HIV therapy for the over 40,000,000 patients afflicted world wide who cannot afford the current HAART therapy.

Initial studies on adults indicate that the following range for unit dosages for each of the ingredients would be appropriate.

Verapamil 5 to 500 mg, preferably 20 to 240 mg
Chloroquine 5 to 1200 mg, preferably 20 to 1200 mg
Quercetin 5 to 500 mg, preferably 10 to 500 mg.

These dosages should be administered 1–4 times a day, preferably one time per day. It is also envisaged that lower dosages may be appropriate for children. The adjustment of the dosages according to body weight and metabolism would be apparent to those skilled in the art.

Any suitable antagonist, generally, of neuronal voltage-dependent Ca. sup.++ channels can be effective under certain conditions. Preferred calcium channel antagonists include, but are not limited to, the following drugs, of which the most preferred are those that are capable of crossing the blood brain barrier, for example, nimodipine (Miles Pharmaceuticals, West Haven, Conn.), Smith Kline drug no. 9512 (Smith Kline, French Beecham, Philadelphia, Pa.), and diproteverine (Smith Kline, French-Beecham). Less preferred antagonists are those that are less CNS permeable, for example, verapamil (Calan, G.D. Searle& Co., Chicago, Ill.; Isoptin, Knoll, Whippany, N.J.), nitrendipine, and diltiazem (Cardizem, Marion, Kansas City, Mo.). Other Ca.sup.2+ channel antagonists which may be useful are mioflazine, flunarizine, bepridil, lidoflazine, CERM-196, R 58735, R-56865, Ranolazine, Nisoldipine, Nicardipine, PN200–110, Felodipine, Amlodipine, R-(−)-202–791, and R-(+) Bay K-8644 (Miles, Bayer), whose chemical formulae are described in Boddeke et al., Trends in Pharmacologic Sciences(1989) 10:397 and Triggle et al., Trends in Pharmnacologic Sciences (1989) 10:370, incorporated by reference.

Verapamil is a known Ca channel blocker and is a competitive inhibitor of P-glycoprotein, as described by Inoue et al. (1993); Hunter et al. (1993); Hori et al. (1993); Pourtier-Manzanedo et al. (1992); Boesch & Loor (1994); Zacherl et al. (1994); Shirai et al. (1991); Morris et al. (1991); Muller et al. (1994); and Miyamoto et al. (1992). Thalhammer et al. (1994) showed that P-glycoprotein-mediated transport of the cationic dye, acridine orange, across the bile canaliculi was inhibited by cyclosporine A and verapamil. The ATP-15 dependent transport of amphiphilic cations across the hepatocyte canalicular membrane by p-glycoprotein was also studied by Muller et al. (1994). Transport of permanently charged amphiphilic cations was inhibited by verapamil, quinidine and daunorubicin (an antibiotic). Bear (1994) showed that verapamil, colchicine, vinblastine daunomycin and (50 microM) blocked an outwardly-rectifying chloride channel that was proposed to be associated with p-glycoprotein expression. Ohi et al. (1992) used the calcium-channel blocker, verapamil, with adriamycin in chemotherapy for superficial bladder cancer. Five ampules (10 ml) of injectable verapamil were given. Verapamil hydrochloride is benzeneacetonitrile α-[3-[[2-(3,4-dimethoxyphenyl)ethyl]-methylamino] propyl]-3,4-dimethoxy-α-(1-methylethyl) hydrochloride; also termed CALAN (TM) and ISOPTIN (TM), and available from Searle, Knoll and Parke-Davis.

It is more than 90% absorbed, but only 20 to 35% of the dose reaches the system because of extensive hepatic first-pass metabolism. It is bound approximately 90% to plasma proteins. It is metabolized rapidly by the liver to norverapamil and traces of several other metabolites. About 70% of a dose is excreted in urine as metabolites, and 16% of a dose appears in the feces within 5 days; less than 5% is excreted unchanged. The effects of verapamil are evident within 30 to 60 minutes of an oral dose. Peak effects of verapamil occur within 15 minutes of its intravenous administration. The half-life is 1.5 to 5 hours in normal persons but may exceed 9 hours during chronic therapy. In patients with cirrhosis of the liver, the half-life may be increased to 14 to 16 hr. The half-life is increased in patients with liver disease, due, in part, to an increased volume of distribution. Saturation kinetics have been observed after repeated doses.

Preferred doses include: intravenous, adults, initially 5 to 10 mg (0.075 to 0.15 mg/kg) over a period of 2 min (3 min in the elderly), followed by 10 mg (0.150 mg/kg) after 30 min, if necessary; children, up to 1 year, initially 0.1 to 0.2 mg/kg over 2 min (with ECG monitoring), repeated after 30 inn, if necessary; 1 to 15 years, initially 0.1 to 0.3 mg/kg, not to exceed 5 mg, repeated after 30 min, if necessary. Oral, adults, 80 mg 3 or 4 times a day or 240 mg once a day in sustained-released form, gradually increased to as much as 480 mg a day, if necessary. Verapamil is available in injectable dosage forms of 5 mg/2 mL and 10 mg/4 mL; tablet dosage forms of 40 mg, 80 mg and 120 mg; and sustained-release tablets of 240 mg.

This invention relates also to pharmaceutical dosage unit forms for systemic administration (oral, topical administration, transdermal including controlled release of medication for long-term treatment or prophylaxis) which are useful in treating mammals, including humans. The term "dosage unit form" as used in this specification and in the claims refers to physically discrete units suitable as unitary dosage for mammalian subjects, each unit containing a predetermined quantity of the essential active ingredients discussed herein, calculated to produce the desired effect in combination with the required pharmaceutical means which adapt said ingredient for systemic administration.

Examples of dosage unit forms in accordance with this invention are tablets, capsules, orally administered liquid preparations in liquid vehicles, suppositories, and dry preparations for the extemporaneous preparation of preparations in a liquid vehicle. Solid diluents or carriers for the solid oral pharmaceutical dosage unit forms are selected from the group consisting of lipids, carbohydrates, proteins and mineral solids, for example, starch, sucrose, kaolin, dicalcium phosphate, gelatin, acacia, corn syrup, corn starch, talc and the like. Capsules, both hard and soft, are formulated with conventional diluents and excipients, for example, edible oils, talc, calcium carbonate, calcium stearate, magnesium stearate and the like. Liquid pharmaceutical preparations for oral administration may be prepared in water or aqueous solutions which advantageously contain suspending agents, such as for example, sodium carboxymethylcellulose, methylcellulose, acacia, polyvinyl pyrrolidone, polyvinyl alcohol and the like.

Such preparations should be stable under the conditions of manufacture and storage, and ordinarily contain in addition to the basic solvent or suspending liquid, preservatives in the nature of bactericidal and fungicidal agents, for example, parabens, chlorobutanol, benzyl alcohol, phenol, thimerosal, and the like. In many cases it is preferable to include isotonic agents, for example, sugars or sodium chloride. Carriers and vehicles include vegetable oils, water, ethanol, and polyols, for example, glycerol, propylene glycol, liquid polyethylene glycol, and the like.

The pharmaceutical dosage unit forms are prepared in accordance with the preceding general description to provide an effective amount of the essential active ingredients per dosage unit form in admixture with the means for adaptation to systemic administration. In general, the unit dose form will contain 3 to 73 percent by weight of the essential active ingredients.

It will be appreciated that the exact dosage of the essential active ingredient constituting an effective amount for treatment of a mammal according to the method of the invention will vary greatly depending on the specific nature of the clinical condition being treated, severity of the condition, species of mammal, age, weight and condition of the mammal, mode of administration of the dosage form and the specific formulation being administered. The exact dose required for a given situation may be determined by administration of a trial dose and observation of the clinical response. In general, an effective amount to be administered will be within a range of from about ~0.1 mg. per kg. to about 50 mg. per kg. of body weight of the recipient, daily. Preferably 0.5 mg./kg. to about 25 mg./kg. daily is provided. In most instances, a single month of administration will effect a noticeable response and bring about the result desired. In cases such as the treatment of immunological conditions however, it may be desirable to repeat the administrations several times daily over longer periods of time.

The following examples are presented for purposes of illustration only and are not intended to be construed as limiting.

EXAMPLE 1

A mixture of the following ingredients was prepared by hand mixing:

| Ingredient | Quantity |
|---|---|
| Verapamil | 20 to 240 mg |
| Chloroquine | 20 to 1200 mg |
| Quercetin | 10 to 500 mg |

One dosage given orally, 1–4, preferably 1–2 times a day is useful in the relief of immuno-deficiency in adult humans provoked by infective disease, or other etiological causes.

When administered to a human adult suffering from HIV, 1 to 4 dosage units daily, the level is adjusted upward to a normal range.

It has been shown that the administration of the above dosage unit mixed 1–4 times (preferably 1 or 2 times) a day is useful in the relief of immuno-deficiency in adult humans provoked by infective disease, or other etiological causes.

EXAMPLE 2

The following were prepared:

| | | | |
|---|---|---|---|
| MP-1:A | 35 µg/ml | Verapamil | (35 µg) |
| MP-1:B | 10 µg/ml | chloroquine | (10 µg) |
| MP-1:C | 4 µg/ml | quercetin | (4 µg) |

MP-1:MIX a combination of all of the above components
MP-1:½ MIX a combination of ½ of the dose of the components The effects of administration of the above after 4 days of administration on the viral load of peripheral blood lymphocytes infected with a laboratory adapted HIV virus are shown in FIG. 1. As can be seen, MP-1: MIX: and MP-1:½ MIX exhibited a synergistic therapeutic effect and surpassed the effectiveness of AZT.

EXAMPLE 3

Figure 2:
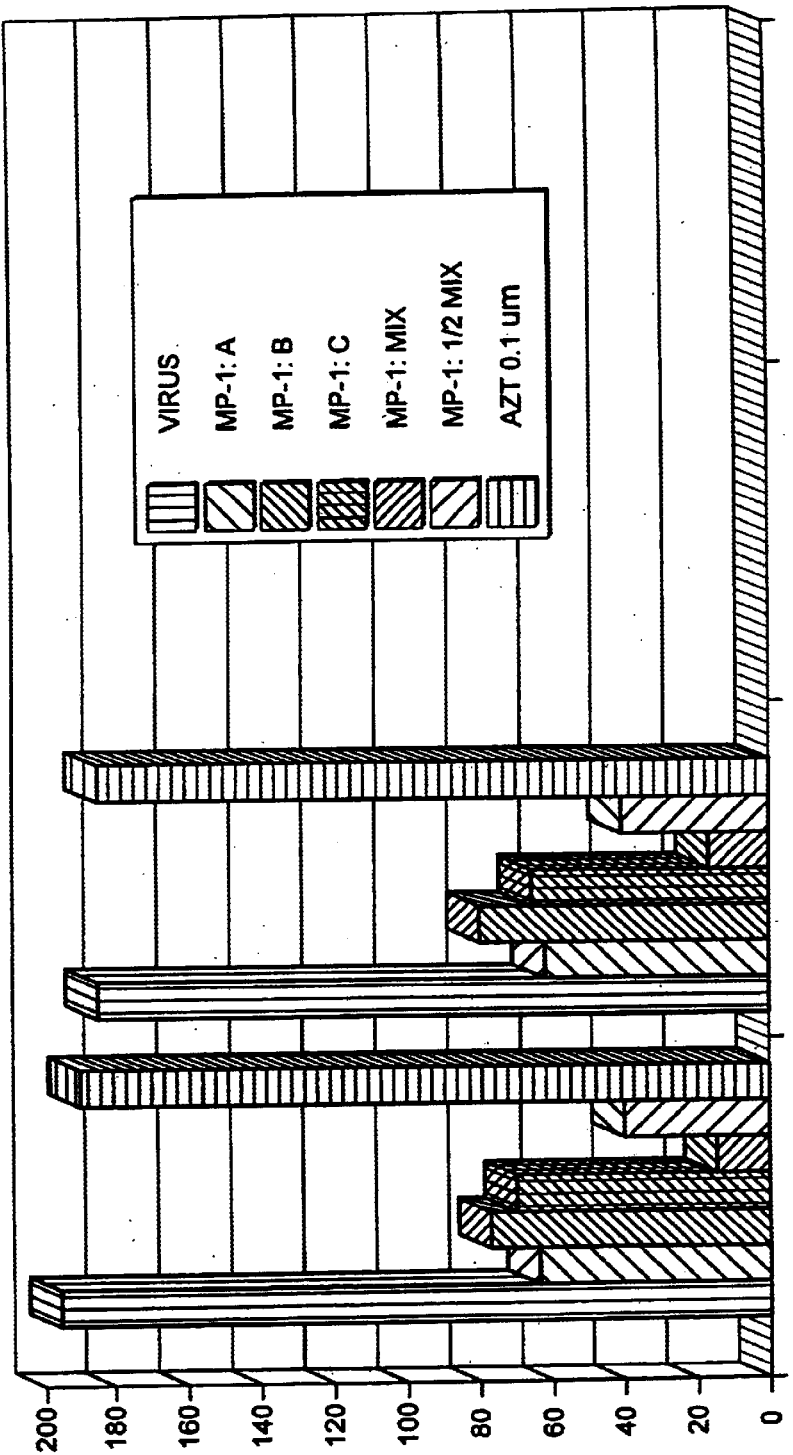
FIG. 2 is a graph depicting the results of 20 experiments on the effects of compositions in accordance with embodiments of the invention, on the viral load (measured by $P_{24}$ ICD) of peripheral blood lymphocytes infected with a HAART resistant clinical viral isolate.

The effects of administration of the above after 4 days of administration on the viral load of peripheral blood lymphocytes infected with a HAART resistant clinical viral isolate are shown in FIG. 2. A synergistic therapeutic effect and superiority to AZT was again demonstrated.

EXAMPLE 4

Figure 3:
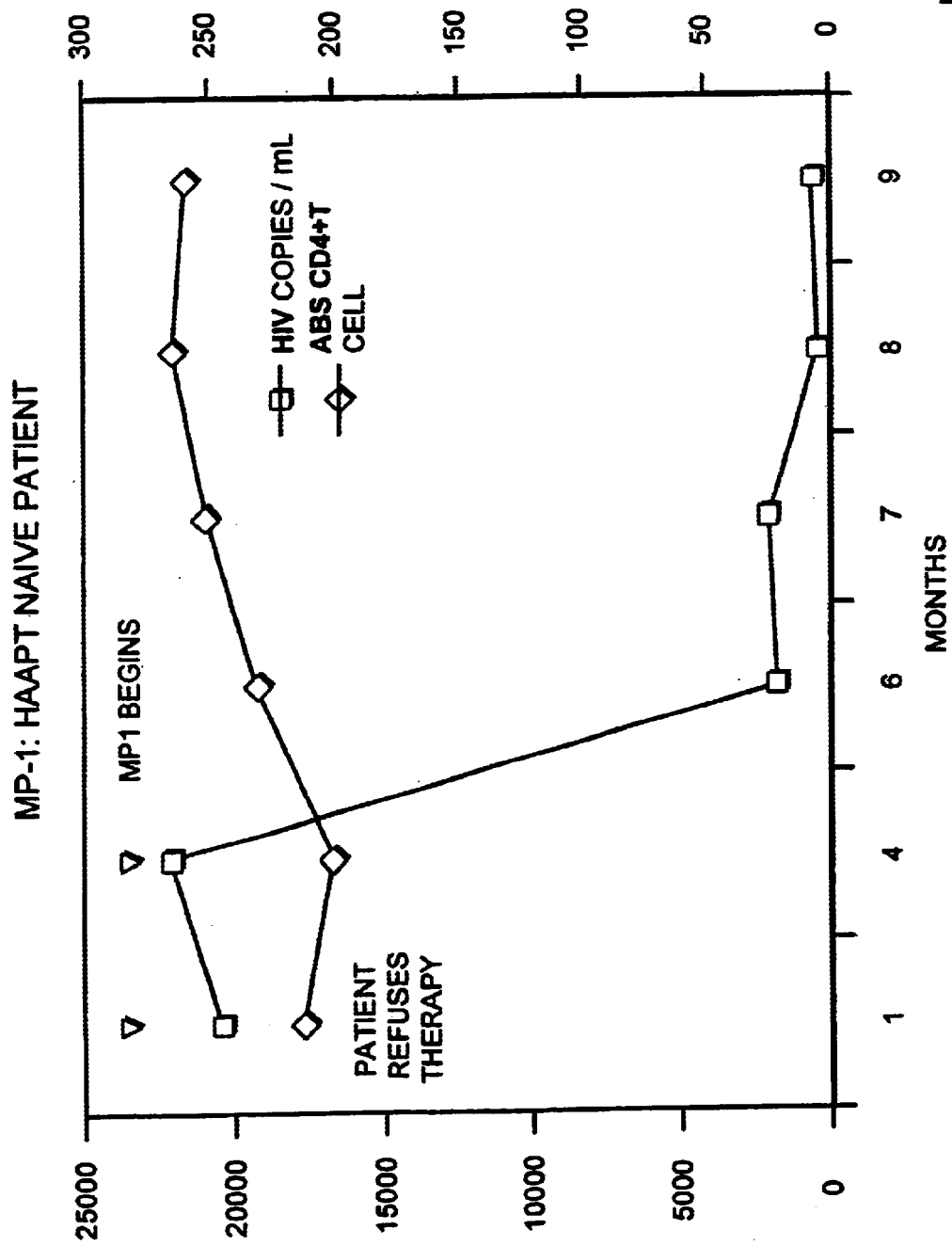
FIG. 3 is a graph showing the effects of verapamil and quercetin on the $CD_4$ count and viral load of a hypertensive patient who refused anti-retroviral therapy.

The effects of verapamil SR 180 and quercetin 150 mg on the $CD_4$ count and viral load of a hypertensive patient who refused anti-retroviral therapy are shown in FIG. 3. Again, the benefits of the invention were demonstrated.

It is understood that the proportions and ingredients may be adjusted for the stage of illness as well as the patient's tolerances of the individual components. Further, it is understood that the metabolites of a calcium channel blocker or quinoline may be used in appropriate forms. Further it is also understood that the active components of quercetin such as polyphenols, glycosides, flavanoids, and bio-flavanoids may be extracted and used in appropriate proportions to yield desired results.

Thus by the present invention its advantages will be realized and preferred embodiments have been disclosed.

What is claimed is:

1. A method of reducing HIV activity in an infected mammal in need thereof, comprising administering to said mammal a therapeutically effective amount of at least one calcium channel blocker and a quinoline or derivatives thereof, in sufficient amounts to treat and reduce HIV activity in said mammal.

2. The method of claim 1, comprising administering quercetin or derivatives thereof, with the channel blocker and quinoline components.

* * * * *